United States Patent
Li et al.

(10) Patent No.: US 9,216,115 B2
(45) Date of Patent: Dec. 22, 2015

(54) SURGICAL TOWEL AND METHOD FOR PRODUCING THE SAME

(71) Applicant: Winner Medical Co., Ltd., Shenzhen (CN)

(72) Inventors: Jianquan Li, Shenzhen (CN); Tao Li, Shenzhen (CN); Haibo Song, Shenzhen (CN); Huifang Xiao, Shenzhen (CN)

(73) Assignee: Winner Medical Co., LTD., Shenzhen (CN)

( * ) Notice: Subject to any disclaimer, the term of this patent is extended or adjusted under 35 U.S.C. 154(b) by 65 days.

(21) Appl. No.: 14/036,108

(22) Filed: Sep. 25, 2013

(65) Prior Publication Data

US 2014/0100541 A1   Apr. 10, 2014

(30) Foreign Application Priority Data

Oct. 8, 2012   (CN) .................. 2012 1 03774005

(51) Int. Cl.
| | |
|---|---|
| *A61F 13/00* | (2006.01) |
| *A61F 13/15* | (2006.01) |
| *D04H 18/00* | (2012.01) |
| *A61F 13/47* | (2006.01) |
| *A61B 19/08* | (2006.01) |
| *D04H 18/04* | (2012.01) |

(52) U.S. Cl.
CPC ......... *A61F 13/15804* (2013.01); *A61B 19/088* (2013.01); *A61F 13/47* (2013.01); *D04H 18/00* (2013.01); *D04H 18/04* (2013.01)

(58) Field of Classification Search
CPC ........... A61B 19/088; A61F 13/15804; D04H 18/04; D04H 1/02; D04H 3/015; D04H 1/492; D04H 1/50; D04H 1/74
See application file for complete search history.

(56) References Cited

U.S. PATENT DOCUMENTS

| | | | | |
|---|---|---|---|---|
| 2,487,197 | A | * | 11/1949 | Stott et al. .......................... 8/650 |
| 5,199,134 | A | * | 4/1993 | Ripley .......................... 19/66 CC |
| 5,253,392 | A | * | 10/1993 | Ripley .......................... 19/66 CC |
| 5,375,306 | A | * | 12/1994 | Roussin-Moynier ........... 28/104 |
| 6,103,061 | A | * | 8/2000 | Anderson et al. ............. 162/108 |
| 2004/0116031 | A1 | * | 6/2004 | Brennan et al. ............... 442/401 |
| 2007/0000064 | A1 | * | 1/2007 | Li ..................................... 8/101 |
| 2008/0023873 | A1 | * | 1/2008 | Mankad et al. ............... 264/180 |

FOREIGN PATENT DOCUMENTS

CN   101624755 A   1/2010

\* cited by examiner

*Primary Examiner* — Lynne Anderson
*Assistant Examiner* — Peter S Vasat
(74) *Attorney, Agent, or Firm* — Alston & Bird LLP

(57) ABSTRACT

Disclosed are a surgical towel and a method for producing the same. The production method includes the following steps: blowing: removing impurities from a pure-cotton raw material; carding: loosening and combing the blown pure-cotton raw material; lapping: spreading cotton-webs, which are formed after the carding, back and forth in the direction of cotton fiber in a staggered overlapping manner; water jetting: water-jet entangling the lapped cotton-webs by using a high-pressure water flow; degreasing: removing wax or grease from cotton fibers of an all-cotton non-woven fabric; bleaching: bleaching the degreased all-cotton non-woven fabric; softening and finishing: softening and finishing the all-cotton non-woven fabric to enhance its softness; and cutting and folding: cutting and folding the softened and finished all-cotton non-woven fabric according to a required specification and packaging the same into a finished product. The surgical towel disclosed in the present application has a strong liquid-absorption capability and soft and comfortable hand-feel, does not easily become fuzzy after rubbing, and can improve safety of a medical surgery.

8 Claims, 2 Drawing Sheets

SURGICAL TOWEL AND METHOD FOR PRODUCING THE SAME

BACKGROUND OF THE INVENTION

1. Field of the Invention

The present application relates to a surgical towel and a method for producing the same.

2. Related Art

Conventional medical gauze surgical towels generally are pure-cotton woven fabrics having relatively low warp and weft densities, which are produced by a procedure including: cotton opening and cleaning-carding-cotton-sliver forming-roving forming-spun yarn forming-warping-slashing-weaving-degreasing and bleaching-dyeing-cutting-manual folding-packaging. The production procedure has disadvantages of having long production process, complex production, high labor cost, high energy consumption, poor production environment, and the like. A medical gauze surgical towel produced through the production procedure is fuzzy on the surface and phenomena such as fiber drop-out, debris fall out and fall-off of thread ends easily occur, making it difficult to ensure medical safety during use in a surgery.

SUMMARY OF THE INVENTION

According to a first aspect of the present application, the present application provides a method for producing a surgical towel, including:

blowing: removing impurities from a pure-cotton raw material;

carding: loosening and combing the blown pure-cotton raw material;

lapping: spreading cotton-webs, which are formed after the carding, back and forth in the direction of cotton fibers in a staggered overlapping manner;

water jetting: water-jet entangling the lapped cotton-webs by using a high-pressure water flow;

degreasing: removing wax or grease from cotton fibers of an all-cotton non-woven fabric;

bleaching: bleaching the degreased all-cotton non-woven fabric;

softening and finishing: softening and finishing the all-cotton non-woven fabric to enhance its softness; and cutting and folding: cutting and folding the softened and finished all-cotton non-woven fabric according to a required specification and packaging the same into a finished product.

According to a second aspect of the present application, the present application provides a surgical towel, which is produced through the above production method.

Beneficial effects of the present application are that: in the method for producing a surgical towel of the present application, a raw material for production of the surgical towel is treated by blowing-carding-lapping-water jetting-degreasing-bleaching. The steps can better remove impurities from the raw material, and the water jetting step can solve the problem of fuzz caused by rubbing during use of the product, thereby improving quality of the product made of the treated raw material. The production method can further save production costs, because the production procedure is simple. In the present application, the raw material for production of the surgical towel is softened and finished to enhance softness of the all-cotton non-woven fabric. Therefore, irritation to a human body when the surgical towel contacts the human body is reduced and safety of a medical surgery can be improved.

DETAILED DESCRIPTION OF THE EMBODIMENTS

The present application is further described below in detail with reference to specific embodiments and accompanying drawings.

Due to rather strict requirements for physicochemical indexes of a surgical towel, and main problems that requirements of hand-feel softness and color fastness can hardly be met when a non-woven fabric having a high weight is used as a surgical towel, a conventional medical gauze surgical towel adopts a pure-cotton woven fabric having lower warp and weft densities.

In an embodiment of the present application, a pure-cotton raw material is treated by blowing-carding-lapping-water jetting-degreasing-bleaching to form an all-cotton non-woven fabric, and the all-cotton non-woven fabric is used as a material for production of a surgical towel. A surgical towel produced by using the all-cotton non-woven fabric contains fewer impurities, and also does not easily become fuzzy after rubbing during use. Meanwhile, the all-cotton non-woven fabric is softened and finished during the production of the surgical towel to enhance its softness, which can reduce irritation to a human body when the surgical towel contacts the human body. Since the complexity and cost of the procedure for producing an all-cotton non-woven fabric are far lower than those of the procedure for producing a woven fabric, the cost of a surgical towel made of an all-cotton non-woven fabric is also far lower than that of a surgical towel made of a woven fabric.

Embodiment 1

Figure 1:
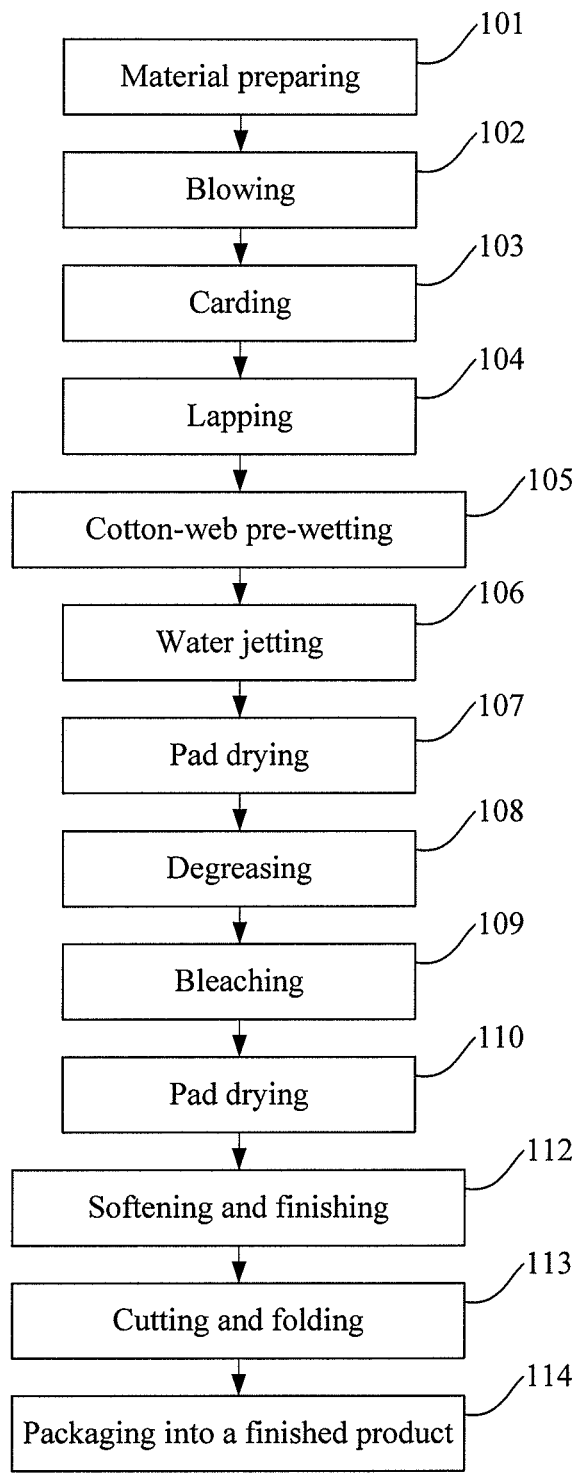
FIG. 1 is a flow chart of steps of a method for producing a surgical towel according to an embodiment of the present application.

Referring to FIG. 1, this embodiment provides a method for producing a surgical towel, which includes the following steps:

Step 101: Material preparing: a pure-cotton raw material is prepared for use, where the pure-cotton raw material refers to natural lint cotton which is neither degreased nor blenched, and the pure-cotton raw material may be treated by simple washing or stewing.

Step 102: Blowing: impurities in the pure-cotton raw material are removed by using a cotton cleaner.

Step 103: Carding: the blown pure-cotton raw material is loosened and combed. The blown pure-cotton raw material is loosened into single-fibers and is combed smoothly in the longitudinal direction of fibers of the pure-cotton raw material by using a carding machine. Through step 103, a maximum tension among the fibers of the pure-cotton raw material can be achieved. Step 103 may be repeated once, twice, or more times according to requirements during the production.

Step 104: Lapping: according to a weight specification requirement of a product, cotton-webs, which are formed after the carding, are spread back and forth in the direction of cotton fibers in a staggered overlapping manner. Through step 104, the tension caused by friction between the cotton fibers can be enhanced to ensure the tensile strength of a final finished product.

Step 105: Cotton-web pre-wetting: the cotton-webs are pre-wet to provide a good moistening condition for step 106.

Step 106: Water jetting: front or back water jetting is performed on the cotton-webs by using a high-pressure water flow, so that the fibers of the pure-cotton raw material are fully entangled to reinforce the tension of the bonded cotton fibers and enhance the tensile strength of the final finished product, and at the same time tiny impurities can be further removed. In a specific example, the water jetting is selected to be performed for three times. By selecting a proper number of times of the water jetting, not only the production cost can be controlled, but also the problem of fuzz caused by rubbing during use of the product can be well solved.

Step 107: Pad drying: water in the cotton-webs after the water jetting is squeezed out.

Step 108: Degreasing: wax or grease on the cotton fibers of the all-cotton non-woven fabric is removed to enhance the water absorbability of the finished product.

Step 109: Bleach: the whiteness of the cotton fibers is improved.

Step 110: Pad drying: water in the bleached all-cotton non-woven fabric is squeezed out.

Step 112: Softening and finishing, which is performed to enhance softness of the all-cotton non-woven fabric. The softening and finishing in step 112 may adopt any one of the following two softening and finishing processes: a mechanical softening and finishing process and a chemical-reagent softening and finishing process.

The mechanical softening and finishing process is kneading and creasing the all-cotton non-woven fabric for several times by using a mechanical method to reduce rigidity of the all-cotton non-woven fabric so that it can restore a proper softness. The mechanical softening and finishing process mainly includes the following steps: forming and drying the all-cotton non-woven fabric, that is, kneading and creasing the all-cotton non-woven fabric for several times under a small mechanical force, so that the cloth cover is wrinkled crosswise, that is, wrinkled in the width direction; and again forming and drying the all-cotton non-woven fabric. The internal stress of the fibers of the all-cotton non-woven fabric can be fully released by means of the mechanical softening and finishing, so that the all-cotton non-woven fabric is softened.

The chemical-reagent softening and finishing process refers to using a chemical softening agent to lower the coefficient of friction between the fibers of the all-cotton non-woven fabric to achieve a softening effect. The chemical-reagent softening and finishing process mainly includes the following steps: immersing the all-cotton non-woven fabric into a solution containing a hydrophilic organosilicone nano-emulsion, then extruding excess liquid by a rubber roller, so that the liquid-containing rate of the cloth cover is 70% to 90%, and then forming and drying the all-cotton non-woven fabric. The chemical-reagent softening and finishing process can enable the all-cotton non-woven fabric to have a soft, plump, and fluffy hand-feel, and also can enable the product to have a good water absorbability.

Step 113: Cutting and folding. The all-cotton non-woven fabric after the softening and finishing is cut and folded according to a required specification. In a specific example, step 113 adopts automatic mechanical cutting and folding, for example, adopts a novel high-speed full-automatic non-woven fabric folder to perform the folding operation. As compared with manual operations, mechanical automation can greatly improve the speed of cutting and folding, thereby achieving reducing the labor cost and improving the production efficiency.

Step 114: The cut and folded all-cotton non-woven fabric is packaged into a surgical towel finished product for medical use.

The heat-moisture treatment by various machines or chemical agents and the effect of the mechanical tension during the production of the all-cotton non-woven fabric not only cause structural deformation of the all-cotton non-woven fabric, but also lead to a stiff and coarse hand-feel. This defect is addressed by the softening and finishing step in this embodiment, so that a softer surgical towel is produced and no irritation will be caused to a human body during use, thereby improving safety of a medical surgery. Meanwhile, mechanical automation is adopted in the cutting and folding step, thereby reducing the labor cost and improving the production efficiency.

Embodiment 2

Figure 2:
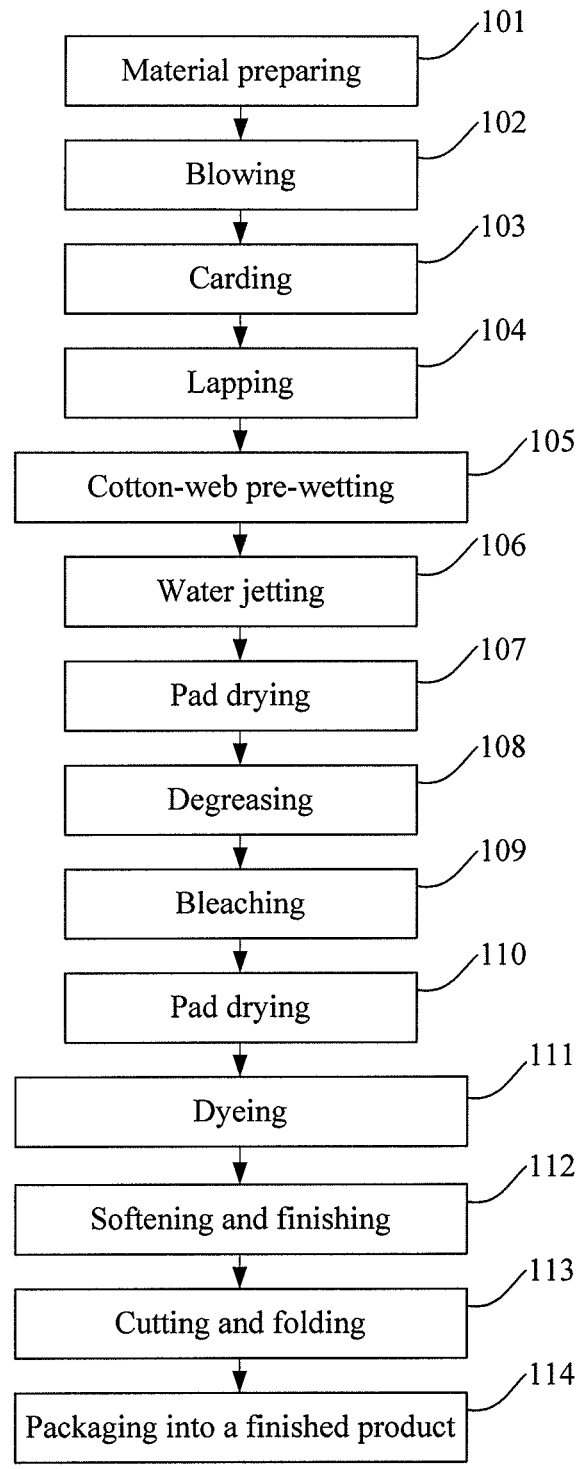
FIG. 2 is a flow chart of steps of a method for producing a surgical towel according to another embodiment of the present application.

Referring to FIG. 2, this embodiment provides another method for producing a surgical towel. A dyeing step 111 is added after the padding step 110 and prior to the softening and finishing step 112 of the above embodiment. In this embodiment, the dyeing step 111 added based on the above embodiment can meet a requirement for producing a surgical towel having a color, for example, blue, green, and the like. The dyeing step 111 may adopt any one of the following two dyeing processes: a reactive-dye cold pad-batch dyeing process and a vat-dye suspension padding process.

The reactive-dye cold pad-batch dyeing process refers to a dyeing method in which the all-cotton non-woven fabric is pad-rolled in reactive-dyes, a dye liquor, and an alkali liquor and roll-pressed by a roller in a low-temperature environment, so that the dye liquor is adsorbed on fiber surfaces of the all-cotton non-woven fabric, and then the all-cotton non-woven fabric is rolled and stacked; and the all-cotton non-woven fabric is stacked at room temperature for a certain period of time and is slowly rotated, so that the process of absorption, diffusion, and color fixation of dyes is completed; and finally washing is performed to complete the dye up-take process. The process mainly includes the following four stages:

working-fluid pad-rolling, where the all-cotton non-woven fabric is pad-rolled in reactive dyes, a dye liquor, and an alkali liquor and roll-pressed by roller at a low temperature, so that the dye liquor is adsorbed on fiber surfaces of the all-cotton non-woven fabric;

stacking and coloring, where the all-cotton non-woven fabric which is pad-rolled in the working fluid is rolled, then is stacked for a predetermined time at room temperature, and is slowly rotated during the stacking;

washing and soaping, where the all-cotton non-woven fabric is washed and soaped according to requirements, where the washing includes washing with warm water, washing with hot water, and/or washing with cold water; and performing color fixation on the dyed all-cotton non-woven fabric by using a color fixing agent.

In a specific example, the specific procedure of the reactive-dye cold pad-batch dyeing process is: degreasing and bleaching an all-cotton non-woven fabric→dye-liquor pad-rolling→rolling and stacking (16-24 hours)→after treatment: feeding into a boiler→washing with warm water→soaping→washing with warm water→washing with hot water→washing with warm water→color fixing→washing with warm water→washing with hot water→washing with cold water and neutralizing→output from the boiler.

The reactive-dye cold pad-batch dyeing process has a short procedure, requires simple equipment, and causes little environmental pollution, and since steps such as drying and steaming are not involved, energy is saved. Meanwhile, the process has advantages such as having a small liquor ratio and a high degree of dyeing (the color fixation rate is increased by 15-25% as compared with that of a conventional pad steaming process) without dye migration, and is especially suitable for dyeing an all-cotton non-woven fabric which is sensitive to the tension and is difficult to be fully dyed.

The vat-dye suspension padding process refers to a dyeing method in which an all-cotton non-woven fabric is immersed into a dye liquor so that the dye liquor fully enters in the all-cotton non-woven fabric under a pressing force of a roller, and then residual liquid is removed. The process mainly includes the following steps:

suspension dye liquor pad-rolling, where the all-cotton non-woven fabric is immersed into the dye liquor, the dye liquor fully enters in the all-cotton non-woven fabric under the pressing force of a roller, and then excess dye liquor is removed;

drying the pad-rolled all-cotton non-woven fabric;

pad-rolling the dried all-cotton non-woven fabric in a reducing solution;

reducing and steaming, in a set temperature and moisture environment, the all-cotton non-woven fabric after being pad-rolled in the reducing solution, so that the dyes are reduced and enter in the interior of the fibers; and washing and oxidizing the reduced and steamed all-cotton non-woven fabric, so that the vat dyes are fixed on surfaces of the cotton fibers, then soaping the same to remove unfixed dyes on the surfaces, and again washing the same to discharge the cloth.

The specific procedure of the vat-dye suspension padding process is: suspension dye liquor pad-rolling→drying→reducing-solution pad-rolling→reducing and steaming→washing→oxidizing→soaping→washing and cloth discharging. The equipment used in the process includes a pad-rolling device, a drying device, a steaming device, and a full-width washing device based on the dyeing procedure.

The pad-rolling device in the vat-dye suspension padding process adopts an evenness calendar. Two ends of a roller of the evenness calendar are pressurized by compressed air, the interior of the roller is pressurized by oil, and the pressure in the whole range is made consistent through adjustment. Therefore, uneven dyeing of the edges and middle part of the all-cotton non-woven fabric is not easily caused. According to situations such as the thickness of an all-cotton non-woven fabric and the dyes, the pad-rolling step may be in the form of immersing once and rolling once, immersing once and rolling twice, immersing twice and rolling twice, or immersing multiple times and rolling once.

The drying device in the vat-dye suspension padding process may adopt infrared-ray drying or hot-air drying. The infrared-ray drying can enable the surface and the interior of the all-cotton non-woven fabric to be evenly heated, and the dyes do not easily migrate from the interior to the surface of the all-cotton non-woven fabric, thereby avoiding uneven dyeing.

The steaming device in the vat-dye suspension padding process may provide a certain temperature and moisture environment for the dyeing process, so that the dyes can be reduced and enter in the interior of the fibers within a short time.

A successive full-width washing machine is adopted in the vat-dye suspension padding process. The successive full-width washing machine adopts a special rotor design to enhance the oscillation washing effect, and with its automatic control system, can reduce the tension of the all-cotton non-woven fabric, has a small drawing force to the product, and meanwhile can ensure washing fastness.

In a specific example, the specific procedure of the vat-dye suspension padding process is: degreasing and bleaching an all-cotton non-woven fabric→suspension dye liquor pad-rolling (one immersing and one rolling, having a liquid-containing rate of 70-90%)→infrared pre-drying→drying by using a drier→reducing-solution pad-rolling→reducing and steaming→washing→washing→oxidizing→soaping→soaping→washing with hot water→washing with cold water→cloth discharging.

The method for producing a surgical towel provided in this embodiment can be used to produce a surgical towel having a color, for example, a blue or green surgical towel. The dyeing method provided in the dyeing step 111 can ensure softness of the all-cotton non-woven fabric to the greatest extent and enable the dyed all-cotton non-woven fabric to have good color fastness. By adding the softening and finishing step after the dyeing step 111, the surgical towel produced through the production method provided in this embodiment can well satisfy the physicochemical indexes of a medical surgical towel.

The above are further detailed descriptions about the present application in combination with specific embodiments, but it cannot be concluded that specific implementation of the present application is merely limited to such descriptions. Persons of ordinary skill in the art also can made simple deductions or replacements without departing from the concept of the present application, which should be regarded as falling within the protection scope of the present application.

What is claimed is:

1. A method for producing a surgical towel, comprising:
   removing impurities from a pure-cotton raw material via blowing;
   carding by loosening and combing the blown pure-cotton raw material;
   lapping the cotton-webs, which are formed after the carding, by spreading back and forth in a direction of cotton fibers in the loosened and combed, blown pure-cotton raw material in a staggered overlapping manner;
   water-jet entangling the lapped cotton-webs by using a high-pressure water flow to form an all-cotton non-woven fabric;
   degreasing the all-cotton non-woven fabric by removing wax or grease from cotton fibers of the all-cotton non-woven fabric;
   bleaching the degreased all-cotton non-woven fabric;
   softening and finishing the all-cotton non-woven fabric to enhance its softness; and
   cutting and folding the softened and finished all-cotton non-woven fabric and packaging the same into a finished product,
   wherein the softening and finishing is chemical-reagent softening and finishing, and
   wherein the chemical-reagent softening and finishing comprises the following steps: immersing the all-cotton non-woven fabric into a solution containing a hydrophilic organosilicone nano-emulsion, then extruding excess liquid by a rubber roller, and then drying and forming the all-cotton non-woven fabric.

2. The method according to claim 1, wherein the softening and finishing includes mechanical softening and finishing.

3. The method according to claim 2, wherein the mechanical softening and finishing comprises the following steps: forming and drying the all-cotton non-woven fabric; kneading and creasing the all-cotton non-woven fabric for several times, so that the all-cotton non-woven fabric is wrinkled crosswise; and again forming and drying the all-cotton non-woven fabric.

4. The production method according to claim 1, further comprising: a cotton-web pre-wetting step after the lapping step and prior to the water jetting step; a step of pad drying the all-cotton non-woven fabric after the water jetting step; and a step of drying the all-cotton non-woven fabric after the bleaching step.

5. The method according to claim 1, further comprising a dyeing step for dyeing the all-cotton non-woven fabric after the bleaching step and prior to the softening and finishing step.

6. The method according to claim 5, wherein the dyeing step adopts a reactive-dye cold pad-batch dyeing process, which comprises the following steps:

working-fluid pad-rolling, wherein the all-cotton non-woven fabric is pad-rolled in reactive dyes, a dye liquor, and an alkali liquor and roll-pressed by roller, so that the dye liquor is adsorbed on fiber surfaces of the all-cotton non-woven fabric;

stacking and coloring, wherein the all-cotton non-woven fabric which is pad-rolled in the working fluid is rolled, then is stacked for a predetermined time at room temperature, and is rotated during the stacking;

washing and soaping, wherein the all-cotton non-woven fabric is washed and soaped, wherein the washing comprises washing with water; and color fixing using a color fixing agent, wherein color fixation is performed on the dyed all-cotton non-woven fabric by using a color fixing agent.

7. The method of claim 6, wherein the washing comprises washing with water having at least one of a first temperature, a second temperature, and a third temperature, wherein the first temperature is greater than the second temperature and the third temperature, wherein the second temperature is greater than the third temperature and the second temperature is less than the first temperature, and wherein the third temperature is less than the first temperature and the second temperature.

8. The production method according to claim 5, wherein the dyeing step adopts a vat-dye suspension padding process, which comprises the following steps:

suspension dye liquor pad-rolling, wherein the all-cotton non-woven fabric is immersed into the dye liquor, the dye liquor fully enters in the all-cotton non-woven fabric under the pressing force of a roller, and then excess dye liquor is removed;

drying the pad-rolled all-cotton non-woven fabric;

pad-rolling the dried all-cotton non-woven fabric in a reducing solution;

reducing and steaming, in a set temperature and moisture environment, the all-cotton non-woven fabric after being pad-rolled in the reducing solution, so that the dyes are reduced and enter in the interior of the fibers; and washing and oxidizing the reduced and steamed all-cotton non-woven fabric, so that the vat dyes are fixed on surfaces of the cotton fibers, then soaping the same to remove unfixed dyes on the surfaces, and again washing the same to discharge the all-cotton non-woven fabric.

\* \* \* \* \*